United States Patent
Koopmann et al.

(10) Patent No.: US 11,273,106 B2
(45) Date of Patent: Mar. 15, 2022

(54) AGENT AND METHOD FOR THE TEMPORARY SHAPING OF KERATINOUS FIBERS

(71) Applicant: Henkel AG & Co. KGaA, Duesseldorf (DE)

(72) Inventors: Nora Koopmann, Hamburg (DE); Anna Puls, Winsen (DE)

(73) Assignee: HENKEL AG & CO. KGAA, Duesseldorf (DE)

( * ) Notice: Subject to any disclaimer, the term of this patent is extended or adjusted under 35 U.S.C. 154(b) by 290 days.

(21) Appl. No.: 15/841,304

(22) Filed: Dec. 14, 2017

(65) Prior Publication Data
US 2018/0168959 A1   Jun. 21, 2018

(30) Foreign Application Priority Data
Dec. 19, 2016  (DE) .................. 10 2016 225 466.9

(51) Int. Cl.
| | |
|---|---|
| *A61K 8/25* | (2006.01) |
| *A61K 8/31* | (2006.01) |
| *A61K 8/34* | (2006.01) |
| *A61Q 5/06* | (2006.01) |
| *A61K 8/39* | (2006.01) |
| *A61K 8/19* | (2006.01) |

(52) U.S. Cl.
CPC .................. *A61K 8/25* (2013.01); *A61K 8/19* (2013.01); *A61K 8/31* (2013.01); *A61K 8/342* (2013.01); *A61K 8/39* (2013.01); *A61Q 5/06* (2013.01)

(58) Field of Classification Search
CPC . A61K 8/25; A61K 8/31; A61K 8/342; A61K 8/39; A61K 8/19; A61Q 5/06
USPC ........................................ 424/70.1
See application file for complete search history.

(56) References Cited

U.S. PATENT DOCUMENTS

| | | | | |
|---|---|---|---|---|
| 5,621,061 A | * | 4/1997 | Hager .................... | C08G 77/12 528/21 |
| 7,485,183 B2 | * | 2/2009 | Hochstein ............. | A61K 8/0262 106/499 |
| 2003/0206872 A1 | | 11/2003 | Halston et al. | |
| 2004/0248762 A1 | * | 12/2004 | McGee ................ | C11B 9/0034 512/21 |
| 2008/0233071 A1 | * | 9/2008 | Hentrich ............. | A61K 8/8182 424/70.122 |
| 2008/0260658 A1 | * | 10/2008 | Winter ................... | A61K 8/042 424/47 |
| 2009/0061004 A1 | * | 3/2009 | Birkel .................... | A61K 8/025 424/489 |
| 2010/0040969 A1 | * | 2/2010 | Bejat .................. | G03G 9/08711 430/111.1 |
| 2010/0158825 A1 | * | 6/2010 | Maesen .................... | A61K 8/26 424/59 |
| 2010/0209376 A1 | * | 8/2010 | Richters ................ | A61K 8/375 424/70.12 |
| 2016/0030304 A1 | | 2/2016 | Nagamatsu et al. | |

FOREIGN PATENT DOCUMENTS

| | | | |
|---|---|---|---|
| DE | 102006053402 A1 | 5/2008 | |
| DE | 102013227119 A1 | 6/2015 | |
| GB | 2550002 A | 11/2017 | |
| JP | 2014172837 A | 9/2014 | |
| WO | 2007073799 A1 | 7/2007 | |
| WO | WO-2008055756 A1 * | 5/2008 | .............. A61K 8/64 |
| WO | 2016030043 A1 | 3/2016 | |

OTHER PUBLICATIONS

Hertl et al., "Reaction of Hexamethyldisilazane with silica", The journal of Physical Chemistry, vol. 75, No. 14, 1971, 2181-2185. (Year: 1971).*
Shirakawa et al., "Palladium-catalyzed silylation of alcohols with hexamethyldisilane", Che, Commun., 2006, 3927-3929. (Year: 2006).*
Ntellectual Property Office, Search Report under Section 17(5) for United Kingdom Patent Application No. GB1721114.5 dated Sep. 2, 2018.
Mintel: "Perfect Clean Cooling Face Wash", Gatsby Skin Tonic, Sep. 2014, http://www.gnpd.com.

* cited by examiner

*Primary Examiner* — Jianfeng Song
(74) *Attorney, Agent, or Firm* — Lorenz & Kopf, LLP

(57) ABSTRACT

Cosmetic compositions or agents and methods for the temporary shaping of keratinous fibers are provided. In an embodiment, a cosmetic composition contains from about 2.0 to about 8.0 wt. % hydrophobized metal oxide powder; from about 0.01 to about 2.0 wt. % carbon-based adsorption agent; from about 3.0 to about 35 wt. % lipid; from about 1.0 to about 10 wt. % emulsifier; and from about 30 to about 50 wt. % water. Embodiments include the use of such cosmetic compositions and methods for employing such compositions.

6 Claims, No Drawings

AGENT AND METHOD FOR THE TEMPORARY SHAPING OF KERATINOUS FIBERS

CROSS-REFERENCE TO RELATED APPLICATION

This application claims priority to German Patent Application No. 10 2016 225 466.9, filed Dec. 19, 2016, which is incorporated herein by reference in its entirety.

TECHNICAL FIELD

The application relates to the technical art of temporary shaping of keratinous fibers, more particularly human hair.

BACKGROUND

Styling agents for deforming keratinous fibers have long been recognized and are used in various forms for creating, refreshing and setting hairstyles which, for many types of hair, can be achieved only using firming active ingredients. Both hair treatment agents that lend the hair a permanent shape, as well as those that lend the hair a temporary shape, play an important role here.

Sprayable products, as well as product formats that are worked into the hairstyle using a comb or the fingers, are suitable for the temporary shaping of keratinous fibers. The latter product group includes oils, as well as waxes, gels, creams and powders.

A current trend in temporary hair shaping is the "undone look" or "out of bed look". A hairstyle in line with this trend appears styled, without the styling agent being immediately apparent, in the form of an oily shine for example. This customer requirement can be realized first and foremost by employing sprays and powders, since such product formats usually contain only small proportions of waxes and oils. However, powders and sprays in particular cannot be applied directly to the hair by employing a comb or the fingers.

A direct application with the fingers, on the other hand, is possible in the case of wax-like hair shaping agents. Although such application offers advantages for individual hair styling, this usually requires the addition of high melting point oils and waxes, which leave behind an oily shine on the hair after use.

BRIEF SUMMARY

Embodiments herein provide cosmetic compositions or agents and methods for the temporary shaping of keratinous fibers. In an embodiment, a cosmetic composition includes from about 2.0 to about 8.0 wt. % hydrophobized metal oxide powder; from about 0.01 to about 2.0 wt. % carbon-based adsorption agent; from about 3.0 to about 35 wt. % lipid; from about 1.0 to about 10 wt. % emulsifier; and from about 30 to about 50 wt. % water.

DETAILED DESCRIPTION

The following detailed description is merely exemplary in nature and is not intended to limit the disclosure or the application and uses of the subject matter as described herein. Furthermore, there is no intention to be bound by any theory presented in the preceding background or the following detailed description.

The present disclosure therefore addressed the problem of providing hair treatment agents for temporary shaping, which achieve a long-lasting style and good remodeling characteristics, but which give the hairstyle a dry and oil-free appearance. In addition, it should be possible to apply the hair treatment agents to the hair using the hands.

It has emerged that these problems can be solved by employing a complex active ingredient mixture to which, as well as other components, hydrophobized metal oxide powder and a carbon-based adsorption means are added.

Hydrophobized metal oxide powder as a component of hair shaping agents are described in the International Application WO 2007/051511 A1, for example.

The use of carbon-based adsorption agents in hair cosmetics for the reductive decoloration is described in German Patent Application DE 10 2006 053 402 A1.

The present application provides:
1. A cosmetic composition, containing:
a) from about 2.0 to about 8.0 wt. % hydrophobized metal oxide powder;
b) from about 0.01 to about 2.0 wt. % carbon-based adsorption agent;
c) from about 3.0 to about 35 wt. % lipid;
d) from about 1.0 to about 10 wt. % emulsifier; and
e) from about 30 to about 50 wt. % water.
2. Cosmetic composition according to Item 1, wherein the compositions, as hydrophobized metal oxide powders, contain a hydrophobized silicate obtained by silanizing pyrogenic silica.
3. Cosmetic composition according to one of the aforementioned items, wherein the composition contains the hydrophobized metal oxide powder relative to its total weight in quantities from about 3.0 to about 7.0 wt. %, such as from about 4.0 to about 6.0 wt. %.
4. Cosmetic composition according to one of the aforementioned items, wherein the composition contains, as the carbon-based adsorbent, charcoal, activated charcoal, carbon black or carbon molecular sieve, such as charcoal or activated charcoal.
5. Cosmetic composition according to one of the aforementioned items, wherein the composition contains the carbon-based adsorbent relative to its total weight in quantities from about 0.05 to about 1.5 wt. %, such as from about 0.1 to about 1.0 wt. %.
6. Cosmetic composition according to one of the aforementioned items, wherein the composition contains the lipid relative to its total weight in quantities from about 5.0 to about 25 wt. %, such as from about 8.0 to about 18 wt. %.
7. Cosmetic composition according to one of the aforementioned points, wherein the composition contains, as the lipid, mineral oil, natural oil, synthetic oil or mixtures thereof.
8. Cosmetic composition according to Item 7, wherein the composition contains mineral oil, natural oil, synthetic oil or mixtures thereof relative to its total weight in quantities from about 0.5 to about 10 wt. %, such as from about 0.5 to about 6.0 wt. %, for example from about 0.5 to about 3.0 wt. %.
9. Cosmetic composition according to one of the aforementioned points, wherein the composition contains, as the lipid, mineral wax, natural wax, synthetic wax or mixtures thereof.
10. Cosmetic composition according to Item 9, wherein the composition contains mineral wax, natural wax, synthetic wax or mixtures thereof relative to its total weight in quantities from about 2.0 to about 25 wt. %, such as from about 4.0 to about 20 wt. %, for example from about 8.0 to about 15 wt. %.
11. Cosmetic composition according to one of the aforementioned points, wherein the composition contains, as the emulsifier, polyoxyalkylenated fatty alcohol, such as ethylene oxide adduct of saturated or unsaturated linear fatty alcohols, each with from about 2 to about 30 mol ethylene oxide per mol of fatty alcohol.

12. Cosmetic composition according to one of the aforementioned items, wherein the composition contains emulsifier relative to its total weight in quantities from about 2.0 to about 8.0 wt. %, such as from about 3.0 to about 7.0 wt. %.

13. Cosmetic composition according to one of the aforementioned items, wherein the composition contains water relative to its total weight in quantities from about 35 to about 50 wt. %, such as from about 40 to about 48 wt. %.

14. Cosmetic composition according to one of the aforementioned items, containing:
a) from about 3.0 to about 7.0 wt. % hydrophobized silicate;
b) from about 0.1 to about 1.0 wt. % charcoal;
c1) from about 0.5 to about 6.0 wt. % mineral oil, natural oil, synthetic oil or mixtures thereof;
c2) from about 4.0 to about 20 wt. mineral wax, natural wax, synthetic wax or mixtures thereof;
d) from about 1.0 to about 10 wt. % ethylene oxide adduct of saturated linear fatty alcohols, each with from about 2 to about 30 mol ethylene oxide per mol fatty alcohol; and
e) from about 30 to about 50 wt. % water.

15. Cosmetic composition according to one of the aforementioned items, wherein the composition exists in the form of hair wax.

16. Use of a cosmetic composition according to one of the items 1 to 15 for the temporary shaping of keratinous fibers.

17. Method for the temporary shaping of keratinous fibers, more particularly human hair, wherein the cosmetic composition according to one of the items 1 to 15 is applied to keratinous fibers.

The agent as contemplated in embodiments herein exists in the form of a hair wax.

A first essential component of the composition as contemplated herein is the hydrophobized metal oxide powder. The addition of the hydrophobized metal oxide powder improves the applicability of the cosmetic composition, the use of which makes it easier to remodel hairstyles with a dry appearance. Exemplary compositions are exemplified in that they contain the hydrophobized metal oxide powder relative to their total weight in quantities from about 3.0 to about 7.0 wt. %, such as from about 4.0 to about 6.0 wt. %. The optimal quantity depends on the proportions by weight of the other components and particularly on the hydrophobicity of the used silica powder.

As contemplated herein, hydrophobized means metal oxides that were modified at least on the surface of the particle in such a manner that the modified particles are moistened by water to a lesser degree than the non-modified particles.

The particle diameter of the primary particles of exemplary hydrophobized metal oxides is less than about 5 μm, such as less than about 1 μm, for example from about 1 to about 50 nm.

As contemplated herein, an exemplary reagent for silanizing the metal oxide is at least one representative from the group formed from silanes, halogen silanes, alkoxysilanes and silazanes. As contemplated herein, exemplary suitable hydrophobized metal oxides of the hydrophobized metal oxide powder are selected from at least one representative of the group formed from hydrophobized silicates, hydrophobized aluminum silicates, hydrophobized titanium dioxide and hydrophobized silica. Hydrophobized silicates have proved to be particularly suitable for producing the cosmetic compositions as contemplated herein, with pyrogenic silica post-treated by silylation or by reacting with polydimethylsiloxane offering particular advantages.

The composition as contemplated in embodiments herein contains, as the hydrophobized metal oxide powder, at least one hydrophobized silica. An exemplary hydrophobized silicas has a specific surface area according to BET of from about 10 to about 400 m$^2$/g, such as from about 40 to about 300 m$^2$/g, for example, from about 80 to about 150 m$^2$/g.

The composition as contemplated in embodiments herein contains, as the hydrophobized metal oxide powder, at least one silanized, hydrophobized silica.

As contemplated herein, an exemplary reagent for silanizing the silica is at least one representative from the group formed from silanes, halogen silanes, alkoxysilanes and silazanes. Exemplary representatives of the group of silanes are hexa($C_1$-$C_{20}$)alkyldisilane, more particularly hexamethyldisilane. Where a halogenosilane is used as the silylating agent, an exemplary halogenosilane is at least one compound from the group formed from the following compounds

[($C_1$-$C_{20}$)Alkyl]$_z$SiX$_{(4-z')}$
X$_3$Si[(CH$_2$)$_n$—R]
X$_2$[($C_1$-$C_{20}$)Alkyl]Si(CH$_2$)$_n$—R
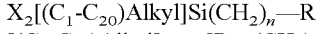
[($C_1$-$C_{20}$)Alkyl]$_{(y'+1)}$[R—(CH$_2$)$_n$]$_{(2-y')}$SiX
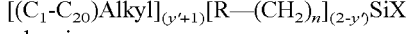

wherein
X means a chlorine, bromine or iodine atom,
z' is a numeral 1, 2 or 3,
y' is a numeral 0, 1 or 2
n is an integer from 1 to 20 and
R denotes a radical from
($C_1$-$C_{10}$)Alkyl-, Aryl-, ($C_1$-$C_6$)Perfluoroalkyl-, —NH$_2$, —N$_3$, —SCN, —CH=CH$_2$, —O(O)C—C(CH$_3$)=CH$_2$, —OCH$_2$—CH=CH$_2$,

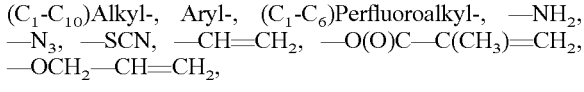

—NH—C(O)O-Me, —NH—C(O)O-Et, —NH—(CH$_2$)$_3$—Si(O($C_1$-$C_6$)alkyl)$_3$.

Where an alkoxysilane is used as the silylating agent, an exemplary alkoxysilane is at least one compound from the group formed from the following compounds

[($C_1$-$C_{20}$)AlkylO]$_z$Si($C_1$-$C_{20}$)Alkyl$_{(4-z)}$
[($C_1$-$C_{20}$)AlkylO]$_z$Si[(CH$_2$)$_n$—R]$_{(4-z)}$
[($C_1$-$C_{20}$)AlkylO]2[($C_1$-$C_{20}$)Alkyl]Si(CH$_2$)$_n$—R
[($C_1$-$C_{20}$)AlkylO][($C_1$-$C_{20}$)Alkyl]2 Si(CH$_2$)$_n$—R
[($C_1$-$C_{20}$)AlkylO][($C_1$-$C_{20}$)Alkyl]Si[(CH$_2$)$_n$—R]$_2$
($C_1$-$C_{20}$Alkyl)$_3$SiO—C(CH$_3$)=N—Si($C_1$-$C_{20}$)Alkyl$_3$,
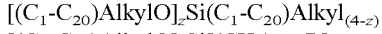
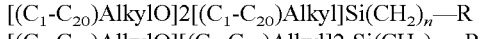
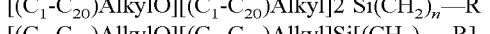
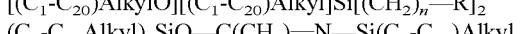
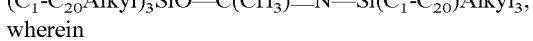

wherein
n is an integer from about 1 to about 20 and
z means a numeral 1, 2, or 3
R denotes a radical from
($C_1$-$C_{20}$)Alkyl-, Aryl-, ($C_1$-$C_6$)Perfluoroalkyl-, —NH$_2$, —N$_3$, —SCN, —CH=CH$_2$, —O(O)C—C(CH$_3$)=CH$_2$, —OCH$_2$—CH=CH$_2$,

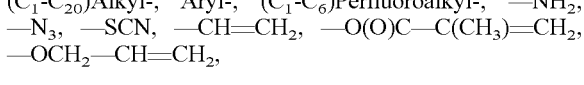

—NH—C(O)O-Me, —NH—C(O)O-Et, —NH—(CH$_2$)$_3$—Si(O($C_1$-$C_6$)alkyl)$_3$.

An exemplary silazane is at least one compound selected from the disilazane class, such as at least one disilazane compound of the formula

wherein
R' means a $(C_1-C_{20})$Alkyl group and
R" means a $(C_1-C_{20})$Alkyl group or a vinyl group. An exemplary silazane is hexamethyldisilazane.

All of the aforementioned alkyl groups, whether $(C_1-C_6)$Alkyl, $(C_1-C_{10})$Alkyl or $(C_1-C_{20})$-Alkyl, can be both cyclical and also linear and/or branched. Examples of alkyl groups suitable for use as contemplated herein are methyl, ethyl, n-Propyl, isopropyl, n-Butyl, cyclopentyl, cyclohexyl, n-Decyl, lauryl, myristyl, cetyl, stearyl, isostearyl and behenyl.

An example of an aryl group as contemplated herein is a phenyl group.

Examples of a $(C_1-C_6)$Perfluoroalkyl group as contemplated herein are trifluormethyl, perfluoroethyl, perfluoropropyl and perfluorohexyl.

An exemplary hydrophobized silica is obtained by silanizing pyrogenic silica. Silanized, hydrophobized silica may be selected from at least one compound of the group formed from trimethylsilylate-coated silica, dimethylsilylate-coated silica, octylsilylate-coated silica.

Exemplary hydrophobized silica is obtained by silanizing pyrogenic silica. Compositions containing, as the hydrophobized metal oxide powder, a hydrophobized silicate obtained by silanizing pyrogenic silica may be preferred due to their product features, more particularly due to their storage stability and their cosmetic effect.

Numerous suitable hydrophobized silicas are commercially available. Examples are Aerosil® R104 V, Aerosil® R106, Aerosil® R202, Aerosil® R805, Aerosil® R812, Aerosil® R812S, Aerosil® R972 and Aerosil® R8200, all from Degussa, as well as HDK® H2000, HDK® H2050 and HDK® H3004, all from Wacker.

Suitable hydrophobized silica is available under the trade names of Aerosil® R202, Aerosil® R812S or Aerosil® R972. An exemplary silica has the INCI designation Silica Silylate, which is sold by Degussa under the trade name of Aerosil® R812S.

Post-treatment with polydimethylsiloxane is an alternative to hydrophobizing by employing silanizing. Compositions as contemplated herein contain a pyrogenic silica post-treated with polydimethylsiloxane. Corresponding metal oxides with the INCI designation "Silica Dimethicone Silylate" are sold by Evonik, for example, under the trade name of Aersoil® R202.

A second essential component of the cosmetic compositions as contemplated herein is the carbon-based adsorbent. Exemplary compositions are exemplified in that they contain the carbon-based adsorbent relative to their total weight in quantities from about 0.05 to about 1.5 wt. %, such as from about 0.1 to about 1.0 wt. %.

Exemplary carbon-based adsorbents are charcoal, activated charcoal, carbon black or carbon molecular sieve, for example charcoal or activated charcoal. In certain embodiments, the adsorbent with the INCI designation Charcoal Powder, which is sold by KPT under the trade name of Charcoal-C Powder 200 is used.

The use of carbon-based adsorbents, more particularly in combination with the hydrophobized metal oxides described above improves the applicability of the cosmetic composition, as well as the holding effect, remodeling characteristics and the dry look. This applies in particular to the exemplary combination of hydrophobized silicate and charcoal and/or activated charcoal.

As contemplated herein, cosmetic compositions contain, as a further component, from about 3.0 to about 35 wt. % of lipid. Limiting the lipid content of the compositions to quantities from about 5.0 to about 25 wt. %, such as from about 8.0 to about 18 wt. %, may be particularly advantageous to the cosmetic effect.

Lipids that are liquid or solid at room temperature (23° C.) are suitable. Compositions containing both liquid and solid lipids may have a particularly advantageous cosmetic effect.

Exemplary cosmetic compositions are exemplified in that they contain a lipid from the group of mineral, natural and synthetic oils or the mixtures thereof.

Triglycerides and the mixtures thereof can be used as natural (plant) oils. Exemplary natural oils are coconut oil, (sweet) almond oil, walnut oil, peach kernel oil, apricot kernel oil, avocado oil, tea tree oil, soya oil, sesame oil, sunflower oil, tsubaki oil, evening primrose oil, rice bran oil, palm kernel oil, mango kernel oil, meadowfoam seed oil, thistle oil, macadamia nut oil, grape seed oil, amaranth seed oil, argan oil, bamboo oil, olive oil, wheatgerm oil, pumpkin seed oil, mallow oil, hazelnut oil, safflower oil, canola oil, sasanqua oil, jojoba oil, rambutan oil, cocoa butter and shea butter.

Silicone compounds are suitable synthetic oils. Suitable silicones can be selected from:
(i) Polyalkylsiloxanes, polyarylsiloxanes, polyalkylarylsiloxanes, which are volatile, non-volatile, straight-chained, branched or cyclical, cross-linked or not cross-linked;
(ii) Polysiloxanes, the general structure of which contains one or more organofunctional groups, are selected from:
a) substituted or unsubstituted aminated groups;
b) (Per)fluorinated groups;
c) thiol groups;
d) carboxylate groups;
e) hydroxylated groups;
f) alkoxylated groups;
g) acyloxyalkyl groups;
h) amphoteric groups;
i) bisulfite groups;
j) hydroxyacylamino groups;
k) carboxy groups;
l) sulfonic acid groups; and
m) sulfate or thiosulfate groups;
(iii) linear polysiloxane(A)-polyoxyalkylene(B)-blockcopolymers of type $(A-B)_n$ where $n>3$;
(iv) grafted silicone polymers with a non-silicone-containing, organic backbone including of an organic main chain, which is formed from organic monomers, which contain no silicone, to which at least one polysiloxane macromer has been grafted within the chain and also, where applicable, to at least one chain end;
(v) grafted silicone polymers with polysiloxane backbone, to which non-silicone-containing, organic monomers have been grafted, which have a polysiloxane main chain, to which at least one organic macromer, which contains no silicone, has been grafted within the chain and also, where applicable, to at least one chain end;
(vi) or the mixtures thereof.

Mineral oils, paraffin and iso-paraffin oils, as well as synthetic hydrocarbons may be used as mineral oils. Exemplary embodiments use paraffins, more particularly liquid paraffins, such as paraffins with the INCI designation Paraffinum Liquidum.

If mineral oils, natural oils, synthetic oils or mixtures thereof are used as the lipid, their percentage by weight of the total weight of the cosmetic composition may be from about 0.5 to about 10 wt. %, such as from about 0.5 to about 6.0 wt. %, for example from about 0.5 to about 3.0 wt. %.

As an alternative to the oils described above or in combination with these oils, exemplary cosmetic compositions contain, as the lipid, mineral wax, natural wax, synthetic wax or mixtures thereof. The percentage by weight of mineral wax, natural wax, synthetic wax of mixtures thereof relative to the total weight of the composition may be from about 2.0 to about 25 wt. %, such as from about 4.0 to about 20 wt. %, for example from about 8.0 to about 15 wt. %.

Exemplary waxes have a melting point in the range from about 40° C. to about 90° C., such as in the range from about 50° C. to about 85° C., for example in the range from about 50° C. to about 75° C.

In principle, all waxes which melt within the stated temperature range and which are physiologically tolerable can be used. Exemplary waxes as contemplated herein are beeswax, carnauba wax, candelilla wax, as well as mineral waxes such as Vaseline, in exemplary embodiments the waxes are beeswax and mineral waxes.

Moreover, a range of wax mixtures, where applicable in admixtures with other additives, are also commercially available. Examples of exemplary mixtures as contemplated herein are those known as "Spezialwachs 7686 OE" (a mixture of cetyl palmitate, beeswax, microcrystalline wax and polyethylene with a melting range from about 73-about 75° C.; manufacturer: Kahl & Co), Polywax® GP 200 (a mixture of stearyl alcohol and polyethylene glycolstearate with a melting point of from about 47 to about 51° C.; manufacturer: Croda) and "Weichceresin® FL 400" (a Vaseline/Vaseline oil/wax mixture with a melting point of from about 50 to about 54° C.; manufacturer: Parafluid Mineralölgesellschaft).

Exemplary cosmetic compositions contain, as the lipid, a mixture of oil and wax. Exemplary embodiments utilize a combination of mineral oil and mineral, as well as natural wax, for example a combination of mineral oil (INCI: Paraffinum Liquidum), vaseline (INCI: Petrolatum) and beeswax (INCI: Cera Alba).

The use of a mixture of oil and wax may be particularly advantageous for the applicability of the cosmetic composition, as well as for the hold and the remodeling characteristics of the temporarily shaped hairstyle.

The fourth essential component of the cosmetic composition as contemplated herein is the emulsifier. The percentage by weight of the emulsifier relative to the total weight of the compositions may be from about 2.0 to about 8.0 wt. %, such as from about 3.0 to about 7.0 wt. %

The exemplary cosmetic agents contain at least one representative from the group of anionic, amphoteric, zwitterionic, non-ionic, cationic emulsifiers or mixtures thereof. Exemplary emulsifiers are solid at room temperature (20° C.), such as non-ionic emulsifiers that are solid at room temperature (20° C.).

An exemplary group of emulsifiers is the polyalkoxylated fatty alcohols, wherein ethylene oxide adduct of saturated or unsaturated linear fatty alcohols, each with from about 2 to about 50 mol of ethylene oxide per mol of fatty alcohol, such as from about 2 to about 30 mol of ethylene oxide per mol of fatty alcohol.

Examples of suitable emulsifiers are linear or branched, saturated or unsaturated $C_{12}$-$C_{30}$ alkanols, each of which are etherified with 1-4 ethylene oxide units per molecule. Exemplary compounds have the INCI designations Steareth-2, Steareth-3, Steareth-4, Ceteth-2, Ceteth-3, Ceteth-4, Myristeth-2, Myristeth-3, Myristeth-4, Laureth-2, Laureth-3, Laureth-4, Trideceth-2, Trideceth-3 and Trideceth-4, as well as the mixtures thereof.

A second group of suitable emulsifiers are linear or branched, saturated or unsaturated $C_{12}$-$C_{30}$ alkanols, each of which are etherified with from about 20 to about 50 ethylene oxide units per molecule. Exemplary emulsifiers are compounds with the INCI designations Laureth-20, Laureth-25, Laureth-30, Laureth-40, Laureth-50, Myreth-20, Myreth-25, Myreth-30, Myreth-40, Myreth-50, Ceteth-20, Ceteth-25, Ceteth-30, Ceteth-40, Ceteth-50, Steareth-20, Steareth-21, Steareth-25, Steareth-30, Steareth-40, Steareth-50, Ceteareth-20, Ceteareth-25, Ceteareth-30, Ceteareth-40, Ceteareth-50, Oleth-20, Oleth-25, Oleth-30, Oleth-40 and Oleth-50.

An exemplary emulsifier mixture includes the emulsifiers Steareth-2 and Steareth-21, to which the emulsifier with the INCI designation Oleth-20 may be added.

The cosmetic compositions as contemplated herein may be based on a hydrous or hydrous-alcoholic carrier. Cosmetic compositions may, relative to their total weight, contain from about 35 to about 50 wt. %, such as from about 40 to about 48 wt. % water.

In summary, exemplary cosmetic compositions contain a) from about 3.0 to about 7.0 wt. % hydrophobized silicate;

b) from about 0.1 to about 1.0 wt. % charcoal;

c1) from about 0.5 to about 6.0 wt. % mineral oil, natural oil, synthetic oil or mixtures thereof;

c2) from about 4.0 to about 20 wt. mineral wax, natural wax, synthetic wax or mixtures thereof;

d) from about 1.0 to about 10 wt. % ethylene oxide adduct of saturated linear fatty alcohols, each with from about 2 to about 30 mol ethylene oxide per mol fatty alcohol; and e) from about 30 to about 50 wt. % water.

Additional nourishing agents may be suitable as other active ingredients and excipients.

As the nourishing agent, the agent can contain at least one protein hydrolysate and/or a derivate thereof, for example. Protein hydrolysates are product mixtures obtained through the acidically, basically or enzymatically catalyzed decomposition of proteins. As contemplated herein, the expression protein hydrolysates also includes total hydrolysates, as well as individual amino acids and the derivatives thereof, as well as mixtures of various amino acids. The molecular weight of the protein hydrolysates usable as contemplated herein is between about 75, the molecular weight for glycine, and about 200.000, such as from about 75 to about 50,000, for example from about 75 to about 20,000 Dalton.

The agent as contemplated herein can also contain, as a nourishing agent a vitamin, a provitamin, a vitamin precursor and/or a derivative thereof. As contemplated herein, such vitamins, provitamins and vitamin precursors are usually assigned to the groups A, B, C, E, F and H.

Other nourishing agents are panthenol, coffein, nicotinamide and sorbitol.

The agent as contemplated herein can also contain, as a nourishing agent, a plant extract, as well as mono- and/or oligosaccharides and/or lipids.

The composition of some other exemplary cosmetic compositions can be found in the table below (values in wt. % relative to the total weight of the cosmetic agent, unless otherwise stated).

|  | Formula 1 | Formula 2 | Formula 3 | Formula 4 | Formula 5 |
| --- | --- | --- | --- | --- | --- |
| Hydrophobized metal oxide | 2.0 to 8.0 | 2.0 to 8.0 | 3.0 to 7.0 | 3.0 to 7.0 | 4.0 to 6.0 |
| Carbon-based adsorbent | 0.01 to 2.0 | 0.01 to 2.0 | 0.05 to 1.5 | 0.05 to 1.5 | 0.1 to 1.0 |
| Solid | 3.0 to 35 | 5.0 to 25 | 5.0 to 25 | 5.0 to 25 | 8.0 to 18 |
| Emulsifier | 1.0 to 10 | 2.0 to 8.0 | 2.0 to 8.0 | 3.0 to 7.0 | 3.0 to 7.0 |
| Water | 30 to 50 | 30 to 50 | 35 to 50 | 35 to 50 | 40 to 48 |
| Optional additives | ad 100 | ad 100 | ad 100 | ad 100 | ad 100 |

|  | Formula 1a | Formula 2a | Formula 3a | Formula 4a | Formula 5a |
| --- | --- | --- | --- | --- | --- |
| Silica Silylate | 2.0 to 8.0 | 2.0 to 8.0 | 3.0 to 7.0 | 3.0 to 7.0 | 4.0 to 6.0 |
| Carbon-based adsorbent | 0.01 to 2.0 | 0.01 to 2.0 | 0.05 to 1.5 | 0.05 to 1.5 | 0.1 to 1.0 |
| Solid | 3.0 to 35 | 5.0 to 25 | 5.0 to 25 | 5.0 to 25 | 8.0 to 18 |
| Emulsifier | 1.0 to 10 | 2.0 to 8.0 | 2.0 to 8.0 | 3.0 to 7.0 | 3.0 to 7.0 |
| Water | 30 to 50 | 30 to 50 | 35 to 50 | 35 to 50 | 40 to 48 |
| Optional additives | ad 100 | ad 100 | ad 100 | ad 100 | ad 100 |

|  | Formula 6 | Formula 7 | Formula 8 | Formula 9 | Formula 10 |
| --- | --- | --- | --- | --- | --- |
| Hydrophobized silicate | 2.0 to 8.0 | 2.0 to 8.0 | 3.0 to 7.0 | 3.0 to 7.0 | 4.0 to 6.0 |
| Carbon-based adsorbent | 0.01 to 2.0 | 0.01 to 2.0 | 0.05 to 1.5 | 0.05 to 1.5 | 0.1 to 1.0 |
| Solid | 3.0 to 35 | 5.0 to 25 | 5.0 to 25 | 5.0 to 25 | 8.0 to 18 |
| Emulsifier | 1.0 to 10 | 2.0 to 8.0 | 2.0 to 8.0 | 3.0 to 7.0 | 3.0 to 7.0 |
| Water | 30 to 50 | 30 to 50 | 35 to 50 | 35 to 50 | 40 to 48 |
| Optional additives | ad 100 | ad 100 | ad 100 | ad 100 | ad 100 |

|  | Formula 6a | Formula 7a | Formula 8a | Formula 9a | Formula 10a |
| --- | --- | --- | --- | --- | --- |
| Silica Silylate | 2.0 to 8.0 | 2.0 to 8.0 | 3.0 to 7.0 | 3.0 to 7.0 | 4.0 to 6.0 |
| Carbon-based adsorbent | 0.01 to 2.0 | 0.01 to 2.0 | 0.05 to 1.5 | 0.05 to 1.5 | 0.1 to 1.0 |
| Solid | 3.0 to 35 | 5.0 to 25 | 5.0 to 25 | 5.0 to 25 | 8.0 to 18 |
| Emulsifier | 1.0 to 10 | 2.0 to 8.0 | 2.0 to 8.0 | 3.0 to 7.0 | 3.0 to 7.0 |
| Water | 30 to 50 | 30 to 50 | 35 to 50 | 35 to 50 | 40 to 48 |
| Optional additives | ad 100 | ad 100 | ad 100 | ad 100 | ad 100 |

|  | Formula 11 | Formula 12 | Formula 13 | Formula 14 | Formula 15 |
| --- | --- | --- | --- | --- | --- |
| Hydrophobized metal oxide | 2.0 to 8.0 | 2.0 to 8.0 | 3.0 to 7.0 | 3.0 to 7.0 | 4.0 to 6.0 |
| Charcoal | 0.01 to 2.0 | 0.01 to 2.0 | 0.05 to 1.5 | 0.05 to 1.5 | 0.1 to 1.0 |
| Solid | 3.0 to 35 | 5.0 to 25 | 5.0 to 25 | 5.0 to 25 | 8.0 to 18 |
| Emulsifier | 1.0 to 10 | 2.0 to 8.0 | 2.0 to 8.0 | 3.0 to 7.0 | 3.0 to 7.0 |
| Water | 30 to 50 | 30 to 50 | 35 to 50 | 35 to 50 | 40 to 48 |
| Optional additives | ad 100 | ad 100 | ad 100 | ad 100 | ad 100 |

|  | Formula 11a | Formula 12a | Formula 13a | Formula 14a | Formula 15a |
| --- | --- | --- | --- | --- | --- |
| Silica Silylate | 2.0 to 8.0 | 2.0 to 8.0 | 3.0 to 7.0 | 3.0 to 7.0 | 4.0 to 6.0 |
| Charcoal | 0.01 to 2.0 | 0.01 to 2.0 | 0.05 to 1.5 | 0.05 to 1.5 | 0.1 to 1.0 |
| Solid | 3.0 to 35 | 5.0 to 25 | 5.0 to 25 | 5.0 to 25 | 8.0 to 18 |
| Emulsifier | 1.0 to 10 | 2.0 to 8.0 | 2.0 to 8.0 | 3.0 to 7.0 | 3.0 to 7.0 |
| Water | 30 to 50 | 30 to 50 | 35 to 50 | 35 to 50 | 40 to 48 |
| Optional additives | ad 100 | ad 100 | ad 100 | ad 100 | ad 100 |

|  | Formula 16 | Formula 17 | Formula 18 | Formula 19 | Formula 20 |
| --- | --- | --- | --- | --- | --- |
| Hydrophobized metal oxide | 2.0 to 8.0 | 2.0 to 8.0 | 3.0 to 7.0 | 3.0 to 7.0 | 4.0 to 6.0 |
| Carbon-based adsorbent | 0.01 to 2.0 | 0.01 to 2.0 | 0.05 to 1.5 | 0.05 to 1.5 | 0.1 to 1.0 |
| Solid* | 3.0 to 35 | 5.0 to 25 | 5.0 to 25 | 5.0 to 25 | 8.0 to 18 |
| Emulsifier | 1.0 to 10 | 2.0 to 8.0 | 2.0 to 8.0 | 3.0 to 7.0 | 3.0 to 7.0 |
| Water | 30 to 50 | 30 to 50 | 35 to 50 | 35 to 50 | 40 to 48 |
| Optional additives | ad 100 | ad 100 | ad 100 | ad 100 | ad 100 |

*at least one solid from the group comprising mineral oil, mineral wax, natural wax

|  | Formula 16a | Formula 17a | Formula 18a | Formula 19a | Formula 20a |
| --- | --- | --- | --- | --- | --- |
| Silica Silylate | 2.0 to 8.0 | 2.0 to 8.0 | 3.0 to 7.0 | 3.0 to 7.0 | 4.0 to 6.0 |
| Carbon-based adsorbent | 0.01 to 2.0 | 0.01 to 2.0 | 0.05 to 1.5 | 0.05 to 1.5 | 0.1 to 1.0 |
| Solid* | 3.0 to 35 | 5.0 to 25 | 5.0 to 25 | 5.0 to 25 | 8.0 to 18 |

-continued

| | | | | | |
|---|---|---|---|---|---|
| Emulsifier | 1.0 to 10 | 2.0 to 8.0 | 2.0 to 8.0 | 3.0 to 7.0 | 3.0 to 7.0 |
| Water | 30 to 50 | 30 to 50 | 35 to 50 | 35 to 50 | 40 to 48 |
| Optional additives | ad 100 | ad 100 | ad 100 | ad 100 | ad 100 |

*at least one solid from the group comprising mineral oil, mineral wax, natural wax

| | Formula 21 | Formula 22 | Formula 23 | Formula 24 | Formula 25 |
|---|---|---|---|---|---|
| Hydrophobized metal oxide | 2.0 to 8.0 | 2.0 to 8.0 | 3.0 to 7.0 | 3.0 to 7.0 | 4.0 to 6.0 |
| Carbon-based adsorbent | 0.01 to 2.0 | 0.01 to 2.0 | 0.05 to 1.5 | 0.05 to 1.5 | 0.1 to 1.0 |
| Solid | 3.0 to 35 | 5.0 to 25 | 5.0 to 25 | 5.0 to 25 | 8.0 to 18 |
| Emulsifier** | 1.0 to 10 | 2.0 to 8.0 | 2.0 to 8.0 | 3.0 to 7.0 | 3.0 to 7.0 |
| Water | 30 to 50 | 30 to 50 | 35 to 50 | 35 to 50 | 40 to 48 |
| Optional additives | ad 100 | ad 100 | ad 100 | ad 100 | ad 100 |

**Ethylene oxide adduct of saturated or unsaturated linear fatty alcohols, each with 2 to 30 mol of ethylene oxide per mol of fatty alcohol

| | Formula 21a | Formula 22a | Formula 23a | Formula 24a | Formula 25a |
|---|---|---|---|---|---|
| Silica Silylate | 2.0 to 8.0 | 2.0 to 8.0 | 3.0 to 7.0 | 3.0 to 7.0 | 4.0 to 6.0 |
| Carbon-based adsorbent | 0.01 to 2.0 | 0.01 to 2.0 | 0.05 to 1.5 | 0.05 to 1.5 | 0.1 to 1.0 |
| Solid | 3.0 to 35 | 5.0 to 25 | 5.0 to 25 | 5.0 to 25 | 8.0 to 18 |
| Emulsifier** | 1.0 to 10 | 2.0 to 8.0 | 2.0 to 8.0 | 3.0 to 7.0 | 3.0 to 7.0 |
| Water | 30 to 50 | 30 to 50 | 35 to 50 | 35 to 50 | 40 to 48 |
| Optional additives | ad 100 | ad 100 | ad 100 | ad 100 | ad 100 |

**Ethylene oxide adduct of saturated or unsaturated linear fatty alcohols, each with from about 2 to about 30 mol of ethylene oxide per mol of fatty alcohol

| | Formula 26 | Formula 27 | Formula 28 | Formula 29 | Formula 30 |
|---|---|---|---|---|---|
| Hydrophobized silicate | 2.0 to 8.0 | 2.0 to 8.0 | 3.0 to 7.0 | 3.0 to 7.0 | 4.0 to 6.0 |
| Charcoal | 0.01 to 2.0 | 0.01 to 2.0 | 0.05 to 1.5 | 0.05 to 1.5 | 0.1 to 1.0 |
| Solid | 3.0 to 35 | 5.0 to 25 | 5.0 to 25 | 5.0 to 25 | 8.0 to 18 |
| Emulsifier | 1.0 to 10 | 2.0 to 8.0 | 2.0 to 8.0 | 3.0 to 7.0 | 3.0 to 7.0 |
| Water | 30 to 50 | 30 to 50 | 35 to 50 | 35 to 50 | 40 to 48 |
| Optional additives | ad 100 | ad 100 | ad 100 | ad 100 | ad 100 |

| | Formula 26a | Formula 27a | Formula 28a | Formula 29a | Formula 30a |
|---|---|---|---|---|---|
| Silica Silylate | 2.0 to 8.0 | 2.0 to 8.0 | 3.0 to 7.0 | 3.0 to 7.0 | 4.0 to 6.0 |
| Charcoal | 0.01 to 2.0 | 0.01 to 2.0 | 0.05 to 1.5 | 0.05 to 1.5 | 0.1 to 1.0 |
| Solid | 3.0 to 35 | 5.0 to 25 | 5.0 to 25 | 5.0 to 25 | 8.0 to 18 |
| Emulsifier | 1.0 to 10 | 2.0 to 8.0 | 2.0 to 8.0 | 3.0 to 7.0 | 3.0 to 7.0 |
| Water | 30 to 50 | 30 to 50 | 35 to 50 | 35 to 50 | 40 to 48 |
| Optional additives | ad 100 | ad 100 | ad 100 | ad 100 | ad 100 |

| | Formula 31 | Formula 32 | Formula 33 | Formula 34 | Formula 35 |
|---|---|---|---|---|---|
| Hydrophobized silicate | 2.0 to 8.0 | 2.0 to 8.0 | 3.0 to 7.0 | 3.0 to 7.0 | 4.0 to 6.0 |
| Carbon-based adsorbent | 0.01 to 2.0 | 0.01 to 2.0 | 0.05 to 1.5 | 0.05 to 1.5 | 0.1 to 1.0 |
| Solid* | 3.0 to 35 | 5.0 to 25 | 5.0 to 25 | 5.0 to 25 | 8.0 to 18 |
| Emulsifier | 1.0 to 10 | 2.0 to 8.0 | 2.0 to 8.0 | 3.0 to 7.0 | 3.0 to 7.0 |
| Water | 30 to 50 | 30 to 50 | 35 to 50 | 35 to 50 | 40 to 48 |
| Optional additives | ad 100 | ad 100 | ad 100 | ad 100 | ad 100 |

*at least one solid from the group comprising mineral oil, mineral wax, natural wax

| | Formula 31a | Formula 32a | Formula 33a | Formula 34a | Formula 35a |
|---|---|---|---|---|---|
| Silica Silylate | 2.0 to 8.0 | 2.0 to 8.0 | 3.0 to 7.0 | 3.0 to 7.0 | 4.0 to 6.0 |
| Carbon-based adsorbent | 0.01 to 2.0 | 0.01 to 2.0 | 0.05 to 1.5 | 0.05 to 1.5 | 0.1 to 1.0 |
| Solid* | 3.0 to 35 | 5.0 to 25 | 5.0 to 25 | 5.0 to 25 | 8.0 to 18 |
| Emulsifier | 1.0 to 10 | 2.0 to 8.0 | 2.0 to 8.0 | 3.0 to 7.0 | 3.0 to 7.0 |
| Water | 30 to 50 | 30 to 50 | 35 to 50 | 35 to 50 | 40 to 48 |
| Optional additives | ad 100 | ad 100 | ad 100 | ad 100 | ad 100 |

*at least one solid from the group comprising mineral oil, mineral wax, natural wax

| | Formula 36 | Formula 37 | Formula 38 | Formula 39 | Formula 40 |
|---|---|---|---|---|---|
| Hydrophobized silicate | 2.0 to 8.0 | 2.0 to 8.0 | 3.0 to 7.0 | 3.0 to 7.0 | 4.0 to 6.0 |
| Carbon-based adsorbent | 0.01 to 2.0 | 0.01 to 2.0 | 0.05 to 1.5 | 0.05 to 1.5 | 0.1 to 1.0 |
| Solid | 3.0 to 35 | 5.0 to 25 | 5.0 to 25 | 5.0 to 25 | 8.0 to 18 |
| Emulsifier** | 1.0 to 10 | 2.0 to 8.0 | 2.0 to 8.0 | 3.0 to 7.0 | 3.0 to 7.0 |

-continued

|   | | | | | |
|---|---|---|---|---|---|
| Water | 30 to 50 | 30 to 50 | 35 to 50 | 35 to 50 | 40 to 48 |
| Optional additives | ad 100 | ad 100 | ad 100 | ad 100 | ad 100 |

**Ethylene oxide adduct of saturated or unsaturated linear fatty alcohols, each with from about 2 to about 30 mol of ethylene oxide per mol of fatty alcohol

|   | Formula 36a | Formula 37a | Formula 38a | Formula 39a | Formula 40a |
|---|---|---|---|---|---|
| Silica Silylate | 2.0 to 8.0 | 2.0 to 8.0 | 3.0 to 7.0 | 3.0 to 7.0 | 4.0 to 6.0 |
| Carbon-based adsorbent | 0.01 to 2.0 | 0.01 to 2.0 | 0.05 to 1.5 | 0.05 to 1.5 | 0.1 to 1.0 |
| Solid | 3.0 to 35 | 5.0 to 25 | 5.0 to 25 | 5.0 to 25 | 8.0 to 18 |
| Emulsifier** | 1.0 to 10 | 2.0 to 8.0 | 2.0 to 8.0 | 3.0 to 7.0 | 3.0 to 7.0 |
| Water | 30 to 50 | 30 to 50 | 35 to 50 | 35 to 50 | 40 to 48 |
| Optional additives | ad 100 | ad 100 | ad 100 | ad 100 | ad 100 |

**Ethylene oxide adduct of saturated or unsaturated linear fatty alcohols, each with from about 2 to about 30 mol of ethylene oxide per mol of fatty alcohol

|   | Formula 41 | Formula 42 | Formula 43 | Formula 44 | Formula 45 |
|---|---|---|---|---|---|
| Hydrophobized silicate | 2.0 to 8.0 | 2.0 to 8.0 | 3.0 to 7.0 | 3.0 to 7.0 | 4.0 to 6.0 |
| Charcoal | 0.01 to 2.0 | 0.01 to 2.0 | 0.05 to 1.5 | 0.05 to 1.5 | 0.1 to 1.0 |
| Solid* | 3.0 to 35 | 5.0 to 25 | 5.0 to 25 | 5.0 to 25 | 8.0 to 18 |
| Emulsifier | 1.0 to 10 | 2.0 to 8.0 | 2.0 to 8.0 | 3.0 to 7.0 | 3.0 to 7.0 |
| Water | 30 to 50 | 30 to 50 | 35 to 50 | 35 to 50 | 40 to 48 |
| Optional additives | ad 100 | ad 100 | ad 100 | ad 100 | ad 100 |

*at least one solid from the group comprising mineral oil, mineral wax, natural wax

|   | Formula 41a | Formula 42a | Formula 43a | Formula 44a | Formula 45a |
|---|---|---|---|---|---|
| Silica Silylate | 2.0 to 8.0 | 2.0 to 8.0 | 3.0 to 7.0 | 3.0 to 7.0 | 4.0 to 6.0 |
| Charcoal | 0.01 to 2.0 | 0.01 to 2.0 | 0.05 to 1.5 | 0.05 to 1.5 | 0.1 to 1.0 |
| Solid* | 3.0 to 35 | 5.0 to 25 | 5.0 to 25 | 5.0 to 25 | 8.0 to 18 |
| Emulsifier | 1.0 to 10 | 2.0 to 8.0 | 2.0 to 8.0 | 3.0 to 7.0 | 3.0 to 7.0 |
| Water | 30 to 50 | 30 to 50 | 35 to 50 | 35 to 50 | 40 to 48 |
| Optional additives | ad 100 | ad 100 | ad 100 | ad 100 | ad 100 |

*at least one solid from the group comprising mineral oil, mineral wax, natural wax

|   | Formula 46 | Formula 47 | Formula 48 | Formula 49 | Formula 50 |
|---|---|---|---|---|---|
| Hydrophobized silicate | 2.0 to 8.0 | 2.0 to 8.0 | 3.0 to 7.0 | 3.0 to 7.0 | 4.0 to 6.0 |
| Charcoal | 0.01 to 2.0 | 0.01 to 2.0 | 0.05 to 1.5 | 0.05 to 1.5 | 0.1 to 1.0 |
| Solid | 3.0 to 35 | 5.0 to 25 | 5.0 to 25 | 5.0 to 25 | 8.0 to 18 |
| Emulsifier** | 1.0 to 10 | 2.0 to 8.0 | 2.0 to 8.0 | 3.0 to 7.0 | 3.0 to 7.0 |
| Water | 30 to 50 | 30 to 50 | 35 to 50 | 35 to 50 | 40 to 48 |
| Optional additives | ad 100 | ad 100 | ad 100 | ad 100 | ad 100 |

**Ethylene oxide adduct of saturated or unsaturated linear fatty alcohols, each with from about 2 to about 30 mol of ethylene oxide per mol of fatty alcohol

|   | Formula 46a | Formula 47a | Formula 48a | Formula 49a | Formula 50a |
|---|---|---|---|---|---|
| Silica Silylate | 2.0 to 8.0 | 2.0 to 8.0 | 3.0 to 7.0 | 3.0 to 7.0 | 4.0 to 6.0 |
| Charcoal | 0.01 to 2.0 | 0.01 to 2.0 | 0.05 to 1.5 | 0.05 to 1.5 | 0.1 to 1.0 |
| Solid | 3.0 to 35 | 5.0 to 25 | 5.0 to 25 | 5.0 to 25 | 8.0 to 18 |
| Emulsifier** | 1.0 to 10 | 2.0 to 8.0 | 2.0 to 8.0 | 3.0 to 7.0 | 3.0 to 7.0 |
| Water | 30 to 50 | 30 to 50 | 35 to 50 | 35 to 50 | 40 to 48 |
| Optional additives | ad 100 | ad 100 | ad 100 | ad 100 | ad 100 |

**Ethylene oxide adduct of saturated or unsaturated linear fatty alcohols, each with from about 2 to about 30 mol of ethylene oxide per mol of fatty alcohol

|   | Formula 46 | Formula 47 | Formula 48 | Formula 49 | Formula 50 |
|---|---|---|---|---|---|
| Hydrophobized silicate | 2.0 to 8.0 | 2.0 to 8.0 | 3.0 to 7.0 | 3.0 to 7.0 | 4.0 to 6.0 |
| Charcoal | 0.01 to 2.0 | 0.01 to 2.0 | 0.05 to 1.5 | 0.05 to 1.5 | 0.1 to 1.0 |
| Solid* | 3.0 to 35 | 5.0 to 25 | 5.0 to 25 | 5.0 to 25 | 8.0 to 18 |
| Emulsifier** | 1.0 to 10 | 2.0 to 8.0 | 2.0 to 8.0 | 3.0 to 7.0 | 3.0 to 7.0 |

-continued

|  | | | | | |
|---|---|---|---|---|---|
| Water | 30 to 50 | 30 to 50 | 35 to 50 | 35 to 50 | 40 to 48 |
| Optional additives | ad 100 | ad 100 | ad 100 | ad 100 | ad 100 |

*at least one solid from the group comprising mineral oil, mineral wax, natural wax
**Ethylene oxide adduct of saturated or unsaturated linear fatty alcohols, each with from about 2 to about 30 mol of ethylene oxide per mol of fatty alcohol

|  | Formula 46a | Formula 47a | Formula 48a | Formula 49a | Formula 50a |
|---|---|---|---|---|---|
| Silica Silylate | 2.0 to 8.0 | 2.0 to 8.0 | 3.0 to 7.0 | 3.0 to 7.0 | 4.0 to 6.0 |
| Charcoal | 0.01 to 2.0 | 0.01 to 2.0 | 0.05 to 1.5 | 0.05 to 1.5 | 0.1 to 1.0 |
| Solid* | 3.0 to 35 | 5.0 to 25 | 5.0 to 25 | 5.0 to 25 | 8.0 to 18 |
| Emulsifier** | 1.0 to 10 | 2.0 to 8.0 | 2.0 to 8.0 | 3.0 to 7.0 | 3.0 to 7.0 |
| Water | 30 to 50 | 30 to 50 | 35 to 50 | 35 to 50 | 40 to 48 |
| Optional additives | ad 100 | ad 100 | ad 100 | ad 100 | ad 100 |

*at least one solid from the group comprising mineral oil, mineral wax, natural wax
**Ethylene oxide adduct of saturated or unsaturated linear fatty alcohols, each with from about 2 to about 30 mol of ethylene oxide per mol of fatty alcohol

|  | Formula 51 | Formula 52 | Formula 53 | Formula 54 | Formula 55 |
|---|---|---|---|---|---|
| Hydrophobized silicate | 2.0 to 8.0 | 2.0 to 8.0 | 3.0 to 7.0 | 3.0 to 7.0 | 4.0 to 6.0 |
| Charcoal | 0.01 to 2.0 | 0.01 to 2.0 | 0.05 to 1.5 | 0.05 to 1.5 | 0.1 to 1.0 |
| Mineral oil | 0.5 to 10 | 0.5 to 10 | 0.5 to 6.0 | 0.5 to 6.0 | 0.5 to 3.0 |
| Mineral and/or natural wax | 2.0 to 25 | 4.0 to 20 | 4.0 to 20 | 4.0 to 20 | 8.0 to 15 |
| Emulsifier ** | 1.0 to 10 | 2.0 to 8.0 | 2.0 to 8.0 | 3.0 to 7.0 | 3.0 to 7.0 |
| Water | 30 to 50 | 30 to 50 | 35 to 50 | 35 to 50 | 40 to 48 |
| Optional additives | ad 100 | ad 100 | ad 100 | ad 100 | ad 100 |

*Ethylene oxide adduct of saturated or unsaturated linear fatty alcohols, each with from about 2 to about 30 mol of ethylene oxide per mol of fatty alcohol

|  | Formula 51a | Formula 52a | Formula 53a | Formula 54a | Formula 55a |
|---|---|---|---|---|---|
| Silica Silylate | 2.0 to 8.0 | 2.0 to 8.0 | 3.0 to 7.0 | 3.0 to 7.0 | 4.0 to 6.0 |
| Charcoal | 0.01 to 2.0 | 0.01 to 2.0 | 0.05 to 1.5 | 0.05 to 1.5 | 0.1 to 1.0 |
| Mineral oil | 0.5 to 10 | 0.5 to 10 | 0.5 to 6.0 | 0.5 to 6.0 | 0.5 to 3.0 |
| Mineral and/or natural wax | 2.0 to 25 | 4.0 to 20 | 4.0 to 20 | 4.0 to 20 | 8.0 to 15 |
| Emulsifier ** | 1.0 to 10 | 2.0 to 8.0 | 2.0 to 8.0 | 3.0 to 7.0 | 3.0 to 7.0 |
| Water | 30 to 50 | 30 to 50 | 35 to 50 | 35 to 50 | 40 to 48 |
| Optional additives | ad 100 | ad 100 | ad 100 | ad 100 | ad 100 |

*Ethylene oxide adduct of saturated or unsaturated linear fatty alcohols, each with from about 2 to about 30 mol of ethylene oxide per mol of fatty alcohol

|  | Formula 56 | Formula 57 | Formula 58 | Formula 59 | Formula 60 |
|---|---|---|---|---|---|
| Hydrophobized silicate | 2.0 to 8.0 | 2.0 to 8.0 | 3.0 to 7.0 | 3.0 to 7.0 | 4.0 to 6.0 |
| Charcoal | 0.01 to 2.0 | 0.01 to 2.0 | 0.05 to 1.5 | 0.05 to 1.5 | 0.1 to 1.0 |
| Mineral oil | 0.5 to 10 | 0.5 to 10 | 0.5 to 6.0 | 0.5 to 6.0 | 0.5 to 3.0 |
| Mineral and/or natural wax | 2.0 to 25 | 4.0 to 20 | 4.0 to 20 | 4.0 to 20 | 8.0 to 15 |
| Emulsifier** | 1.0 to 10 | 2.0 to 8.0 | 2.0 to 8.0 | 3.0 to 7.0 | 3.0 to 7.0 |
| Water | 30 to 50 | 30 to 50 | 35 to 50 | 35 to 50 | 40 to 48 |
| Optional additives | ad 100 | ad 100 | ad 100 | ad 100 | ad 100 |

**At least one emulsifier from the group of emulsifiers with the INCI designation Steareth-2 Steareth-21 and Oleth-20

|  | Formula 56a | Formula 57a | Formula 58a | Formula 59a | Formula 60a |
|---|---|---|---|---|---|
| Silica Silylate | 2.0 to 8.0 | 2.0 to 8.0 | 3.0 to 7.0 | 3.0 to 7.0 | 4.0 to 6.0 |
| Charcoal | 0.01 to 2.0 | 0.01 to 2.0 | 0.05 to 1.5 | 0.05 to 1.5 | 0.1 to 1.0 |
| Mineral oil | 0.5 to 10 | 0.5 to 10 | 0.5 to 6.0 | 0.5 to 6.0 | 0.5 to 3.0 |
| Mineral and/or natural wax | 2.0 to 25 | 4.0 to 20 | 4.0 to 20 | 4.0 to 20 | 8.0 to 15 |

-continued

|  | | | | | |
|---|---|---|---|---|---|
| Emulsifier** | 1.0 to 10 | 2.0 to 8.0 | 2.0 to 8.0 | 3.0 to 7.0 | 3.0 to 7.0 |
| Water | 30 to 50 | 30 to 50 | 35 to 50 | 35 to 50 | 40 to 48 |
| Optional additives | ad 100 | ad 100 | ad 100 | ad 100 | ad 100 |

**At least one emulsifier from the group of emulsifiers with the INCI designation Steareth-2 Steareth-21 and Oleth-20

|  | Formula 61 | Formula 62 | Formula 63 | Formula 64 | Formula 65 |
|---|---|---|---|---|---|
| Hydrophobized silicate | 2.0 to 8.0 | 2.0 to 8.0 | 3.0 to 7.0 | 3.0 to 7.0 | 4.0 to 6.0 |
| Charcoal | 0.01 to 2.0 | 0.01 to 2.0 | 0.05 to 1.5 | 0.05 to 1.5 | 0.1 to 1.0 |
| Paraffinum Liquidum | 0.5 to 10 | 0.5 to 10 | 0.5 to 6.0 | 0.5 to 6.0 | 0.5 to 3.0 |
| Petrolatum and Cera Alba | 2.0 to 25 | 4.0 to 20 | 4.0 to 20 | 4.0 to 20 | 8.0 to 15 |
| Emulsifier** | 1.0 to 10 | 2.0 to 8.0 | 2.0 to 8.0 | 3.0 to 7.0 | 3.0 to 7.0 |
| Water | 30 to 50 | 30 to 50 | 35 to 50 | 35 to 50 | 40 to 48 |
| Optional additives | ad 100 | ad 100 | ad 100 | ad 100 | ad 100 |

**At least one emulsifier from the group of emulsifiers with the INCI designation Steareth-2 Steareth-21 and Oleth-20

|  | Formula 61a | Formula 62a | Formula 63a | Formula 64a | Formula 65a |
|---|---|---|---|---|---|
| Silica Silylate | 2.0 to 8.0 | 2.0 to 8.0 | 3.0 to 7.0 | 3.0 to 7.0 | 4.0 to 6.0 |
| Charcoal | 0.01 to 2.0 | 0.01 to 2.0 | 0.05 to 1.5 | 0.05 to 1.5 | 0.1 to 1.0 |
| Paraffinum Liquidum | 0.5 to 10 | 0.5 to 10 | 0.5 to 6.0 | 0.5 to 6.0 | 0.5 to 3.0 |
| Petrolatum and Cera Alba | 2.0 to 25 | 4.0 to 20 | 4.0 to 20 | 4.0 to 20 | 8.0 to 15 |
| Emulsifier** | 1.0 to 10 | 2.0 to 8.0 | 2.0 to 8.0 | 3.0 to 7.0 | 3.0 to 7.0 |
| Water | 30 to 50 | 30 to 50 | 35 to 50 | 35 to 50 | 40 to 48 |
| Optional additives | ad 100 | ad 100 | ad 100 | ad 100 | ad 100 |

**At least one emulsifier from the group of emulsifiers with the INCI designation Steareth-2 Steareth-21 and Oleth-20

As initially stated, the cosmetic compositions as contemplated herein are particularly suitable for the temporary shaping of keratinous fibers. Use of the compositions described above for the temporary shaping of keratinous fibers is therefore a further subject matter of this application.

The temporary shaping of keratinous fibers includes the essential step of applying the cosmetic composition as contemplated herein to the keratinous fibers. A method for the temporary shaping of keratinous fibers, more particularly human hair, wherein the cosmetic composition is applied to keratinous fibers, is therefore likewise a subject matter of this application.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

The invention claimed is:

1. A cosmetic composition consisting of:
    a) from about 2.0 to about 8.0 wt. % hydrophobized metal oxide powder;
    b) from about 0.01 to about 2.0 wt. % carbon-based adsorption agent;
    c) from about 3.0 to about 35 wt. % lipid;
    d) from about 1.0 to about 10 wt. % emulsifier;
    e) from about 30 to about 50 wt. % water; and
    f) a nourishing agent or agents selected from protein hydrolysates and/or derivates thereof; vitamins, provitamins, vitamin precursors and/or derivatives thereof; panthenol; coffein; nicotinamide; sorbitol; plant extracts; and/or mono- and/or oligosaccharides.

2. The cosmetic composition according to claim 1, wherein the hydrophobized metal oxide powder is a hydrophobized silicate obtained by silanizing pyrogenic silica.

3. The cosmetic composition according to claim 1, wherein the carbon-based adsorption agent is charcoal, activated charcoal, carbon black or carbon molecular sieve.

4. The cosmetic composition according to claim 1, wherein the
    wherein the hydrophobized metal oxide powder is a hydrophobized silicate
    wherein the carbon-based adsorption agent is charcoal
    wherein the lipid includes mineral oil, natural oil, synthetic oil or mixtures thereof, and mineral wax, natural wax, synthetic wax or mixtures thereof;
    wherein the emulsifier is ethylene oxide adduct of saturated linear fatty alcohols, each with 2 to 30 mol ethylene oxide per mol fatty alcohol.

5. The cosmetic composition according to claim 1 wherein the hydrophobized metal oxide powder is at least one compound selected from the group consisting of trimethylsilylate-coated silica, dimethyl silylate-coated silica, hexamethyldisilane-coated silica, or octylsilylate-coated silica.

6. A method for the temporary shaping of keratinous fibers comprising applying the cosmetic composition according to claim 1 to the keratinous fibers.

* * * * *